(12) United States Patent
Ushiba et al.

(10) Patent No.: US 11,957,475 B2
(45) Date of Patent: Apr. 16, 2024

(54) BIOMETRIC INFORMATION PROCESSING DEVICE, BIOMETRIC INFORMATION PROCESSING METHOD AND PROGRAM

(71) Applicant: Keio University, Tokyo (JP)

(72) Inventors: Junichi Ushiba, Yokohama (JP); Fumio Liu, Tokyo (JP); Kenichi Takasaki, Yokohama (JP); Atsuko Nishimoto, Tokyo (JP); Miho Hiramoto, Tokyo (JP); Katsuhiro Mizuno, Tokyo (JP); Meigen Liu, Tokyo (JP); Toshiyuki Fujiwara, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 926 days.

(21) Appl. No.: 16/300,631

(22) PCT Filed: May 15, 2017

(86) PCT No.: PCT/JP2017/018216
§ 371 (c)(1),
(2) Date: Apr. 15, 2019

(87) PCT Pub. No.: WO2017/195903
PCT Pub. Date: Nov. 16, 2017

(65) Prior Publication Data
US 2020/0237250 A1 Jul. 30, 2020

(30) Foreign Application Priority Data

May 13, 2016 (JP) .................................. 2016-097345

(51) Int. Cl.
*A61B 5/372* (2021.01)
*A61B 5/00* (2006.01)
(Continued)

(52) U.S. Cl.
CPC .............. *A61B 5/375* (2021.01); *A61B 5/316* (2021.01); *A61B 5/377* (2021.01); *A61B 5/4848* (2013.01);
(Continued)

(58) Field of Classification Search
None
See application file for complete search history.

(56) References Cited

U.S. PATENT DOCUMENTS 5,638,826 A * 6/1997 Wolpaw .................. G06F 3/015
340/4.11
2005/0131311 A1 * 6/2005 Leuthardt ............... G06F 3/015
600/545

(Continued)

FOREIGN PATENT DOCUMENTS

JP 2012217721 A 11/2012
JP 2014104549 A 6/2014
(Continued)

OTHER PUBLICATIONS

Neuper et al. ERD/ERS patterns reflecting sensorimotor activation and deactivation. Progress in Brain Research, vol. 159. (Year: 2006).*
(Continued)

*Primary Examiner* — Etsub D Berhanu
(74) *Attorney, Agent, or Firm* — J-TEK LAW PLLC; Jeffrey D. Tekanic; Scott T. Wakeman

(57) ABSTRACT

A biometric information processing device (1) includes a brain wave detecting unit (10), a control unit (20), and a movement assisting unit (30). The brain wave detecting unit (10) detects biometric information in at least one brain region from among a plurality of brain regions that are selectable in accordance with a body part that is a target of function recovery or function improvement. The control unit (Continued)

(20) determines, based on the detected biometric information, at least one activity state in the brain including the location of the brain region(s) that is (are) activated in a subject while attempting to move the body part, and an activation level of such activated brain region(s). When the control unit (20) determines that the at least one activated state of the brain satisfies a predetermined condition, the movement assisting unit (30) executes a predetermined motion to assist movement of the body part.

20 Claims, 14 Drawing Sheets

(51) Int. Cl.
    *A61B 5/316*    (2021.01)
    *A61B 5/375*    (2021.01)
    *A61B 5/377*    (2021.01)
    *A61F 2/72*     (2006.01)
    *G06F 3/01*     (2006.01)

(52) U.S. Cl.
    CPC .............. *A61F 2/72* (2013.01); *G06F 3/015* (2013.01); *A61B 2505/09* (2013.01)

(56) References Cited

U.S. PATENT DOCUMENTS

| | | | |
|---|---|---|---|
| 2009/0259338 | A1 | 10/2009 | Tong et al. |
| 2009/0306531 | A1 | 12/2009 | Leuthardt et al. |
| 2014/0277582 | A1 | 9/2014 | Leuthardt et al. |
| 2014/0330394 | A1 | 11/2014 | Leuthardt et al. |
| 2015/0091791 | A1* | 4/2015 | Segal .................. G06F 16/636 345/156 |
| 2017/0304084 | A1 | 10/2017 | Leuthardt et al. |

FOREIGN PATENT DOCUMENTS

| | | |
|---|---|---|
| WO | 2008151291 A1 | 12/2008 |
| WO | 2011037991 A1 | 3/2011 |

OTHER PUBLICATIONS

Huang et al. Electroencephalography (EEG)-based brain-computer interface (BCI): a 2-D virtual wheelchair control based on event-related desynchronization/synchronization and state control. Apr. 2012. (Year: 2012).*

Bundy. Human Ipsilateral Motor Physiology and Neuroprosthetic Applications in Chronic Stroke. May 2015. (Year: 2015).*

Wisneski et al. Unique Cortical Physiology Associated with Ipsilateral Hand Movements and Neuroprosthetic Implications. 2008. (Year: 2008).*

Yuan et al. Cortical Imaging of Event-Related (de)Synchronization During Online Control of Brain-Computer Interface Using Minimum-Norm Estimates in Frequency Domain. IEEE Transactions on Neural Systems and Rehabilitation Engineering, vol. 16, No. 5, Oct. 2008. (Year: 2008).*

English translation of International Preliminary Report on Patentability dated Nov. 9, 2018 for parent application No. PCT/JP2017/018216.

English translation of International Search Report dated Nov. 16, 2017 for parent application No. PCT/JP2017/018216.

Takashi Ono, A Study on Brain-Machine Interface Rehabilitation for Stroke Hemiplegia, Graduate School of Science and Technology Keio University, [online], Mar. 2015, [retrieval date Jul. 13, 2017], Internet: , Chapter 2, Chapter 5, Figure 2-2.

Machine translation of Written Opinion dated Jul. 25, 2017 for parent application No. PCT/JP2017/018216.

David T. Bundy et al., "Using ipsilateral motor signals in the unaffected cerebral hemisphere as a signal platform for brain computer interfaces in hemiplegic stroke survivors", Journal of Neural Engineering, Institute of Physics Publishing, Bristol, GB, vol. 9, No. 3, May 22, 2012, p. 36011, XP020224621.

Extended European Search Report dated Dec. 5, 2019 in related European Patent Application No. 17796261.0, Including European Search Opinion, Supplementary European Search Report and examined claims 1-14.

Gert Pfurtscheller et al., "Rehabilitation with Brain-Computer Interface Systems", Computer, IEEE Computer Society, USA, vol. 41, No. 10, Oct. 1, 2008, pp. 58-65, XP011236099.

K. Hasegawa et al., Ipsilateral EEG mu rhythm reflects the excitability of uncrossed pathways projecting to shoulder muscles, Journal of NeuroEngineering and Rehabilitation (Aug. 25, 2017) 14:85.

K. Takasaki et al., EEG-based neurofeedback training with shoulder exoskeleton robot assistance triggered by the contralesional primary motor cortex activity in poststroke patients with severe chronic hemiplegia, Oral abstracts / Annals of Physical and Rehabilitation Medicine 61S (2018) e1-e102, ISPR8-1564.

* cited by examiner

FIG. 10
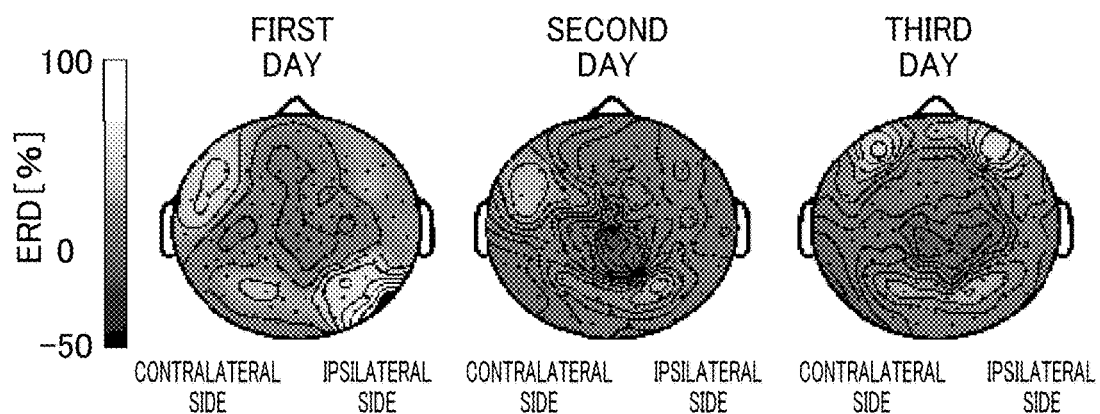
FIG. 11
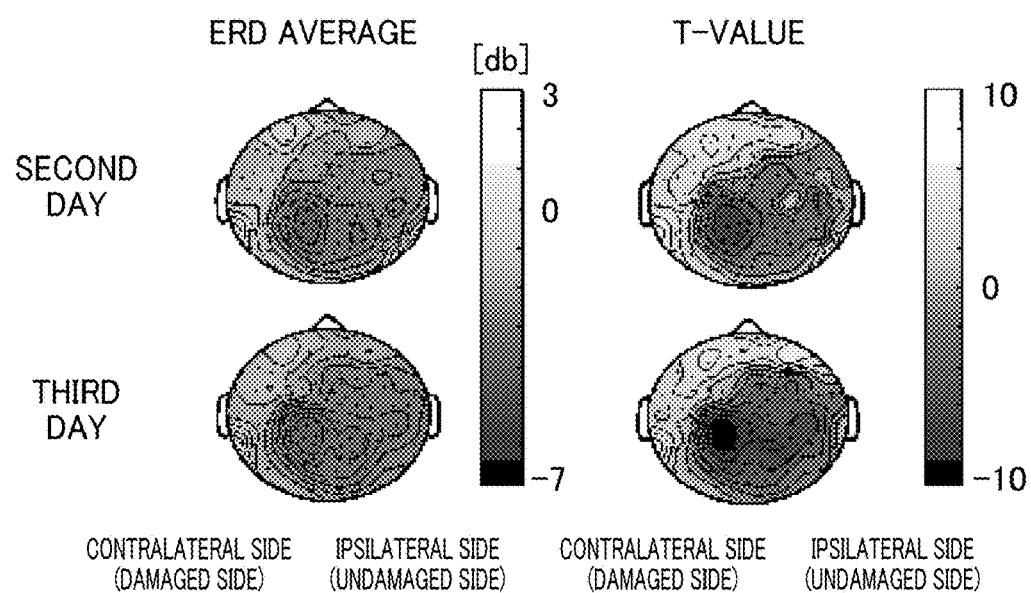
FIG. 12
| | FMA | SIAS (KNEE, MOUTH) | SIAS (FINGER) | MAS (SHOULDER) | RANGE OF POSITIVE MOTION OF SHOULDER BENDING(DEGREE ± SD) | RANGE OF PASSIVE MOTION OF SHOULDER BENDING(DEGREE) |
|---|---|---|---|---|---|---|
| BEFORE THERAPY | 52 | 3 | 2 | 1 | 97.6±2.3 | 108.5 |
| AFTER THERAPY | 57 | 3 | 2 | 1 | 111.6±4.8 | 122 |

FMA-U/E

BIOMETRIC INFORMATION PROCESSING DEVICE, BIOMETRIC INFORMATION PROCESSING METHOD AND PROGRAM

CROSS-REFERENCE

This application is the US national stage of International Patent Application No. PCT/JP2017/018216 filed on May 15, 2017, which claims priority to Japanese Patent Application No. 2016-097345 filed on May 13, 2016.

TECHNICAL FIELD

The present invention relates to a biometric information processing device, a biometric information processing method, and a program.

BACKGROUND ART

In the past, a technique is known that attempts recovery from paralysis in which rehabilitation is performed on hemiplegic patients owing to a stroke using a brain-machine interface (BMI).

For example, in Patent Document 1, a technique for rehabilitation with an exoskeleton robot using a BMI is disclosed.

PRIOR ART DOCUMENT

Patent Document

Patent Document 1: Japanese Unexamined Patent Application, Publication No. 2014-104549

DISCLOSURE OF THE INVENTION

Nevertheless, in the conventional technique for rehabilitation using a BMI, as long as recovery from hemiplegia can be achieved by activating a brain nerve pathway connected to a hemiplegic body part, the purpose of the rehabilitation is regarded as being attained. However, there may be multiple brain nerve pathways that are connected to the hemiplegic body part remaining; in such cases, to pursue the recovery of the entire body of a patient, it is important to restore all brain nerve pathways to restore the hemiplegic body part. For example, in patients who are hemiplegic in the left finger(s) and left shoulder, if a brain nerve pathway connected to a specific brain region in the right brain is activated to rehabilitate the hemiplegic left shoulder, and if the left finger(s) is (are) connected only to the same brain region via the brain nerve pathway, it is difficult to foster rehabilitation from paralysis with respect to the left finger, because resources of the brain region will compete.

That is, in the conventional technique, it was difficult to select and train an appropriate brain region that causes a body part to function.

It is an object of the present invention to be able to select and train an appropriate brain region that causes a body part to function.

In one non-limiting aspect of the present teachings, a biometric information processing device may include:
- a biometric information detecting unit that detects biometric information from at least one brain region from among a plurality of brain regions that are selectable in accordance with the body part that is to become a target of function recovery or function improvement;
- a determination unit (e.g., an information processor) that determines, based on the biometric information from the brain region(s) detected by the biometric information detecting unit, one or more activated states in the brain including location(s) of the brain region(s) that is (are) activated in a test subject attempting movement of said body part and an activation level of said brain region(s); and
- an output unit (e.g., a movement assisting device) that executes a predetermined motion when it is determined by the determination unit that the activated state(s) in the brain conform(s) to a predetermined condition.

According to the present invention, it is possible to select and train an appropriate brain region that causes a body part to function.

BRIEF DESCRIPTION OF THE DRAWINGS

FIG. 10 is a diagram showing changes in brain waves of one non-handicapped person before and after shoulder elevation BMI training was conducted for three consecutive days.

FIG. 11 is a graph showing changes in brain waves in one hemiplegic patient before and after shoulder elevation BMI training was conducted for three consecutive days.

FIG. 12 is a diagram showing results of clinical indicators for one hemiplegic patient before and after shoulder elevation BMI training was conducted for three consecutive days.

DETAILED DESCRIPTION OF THE EMBODIMENTS

Figure 1:
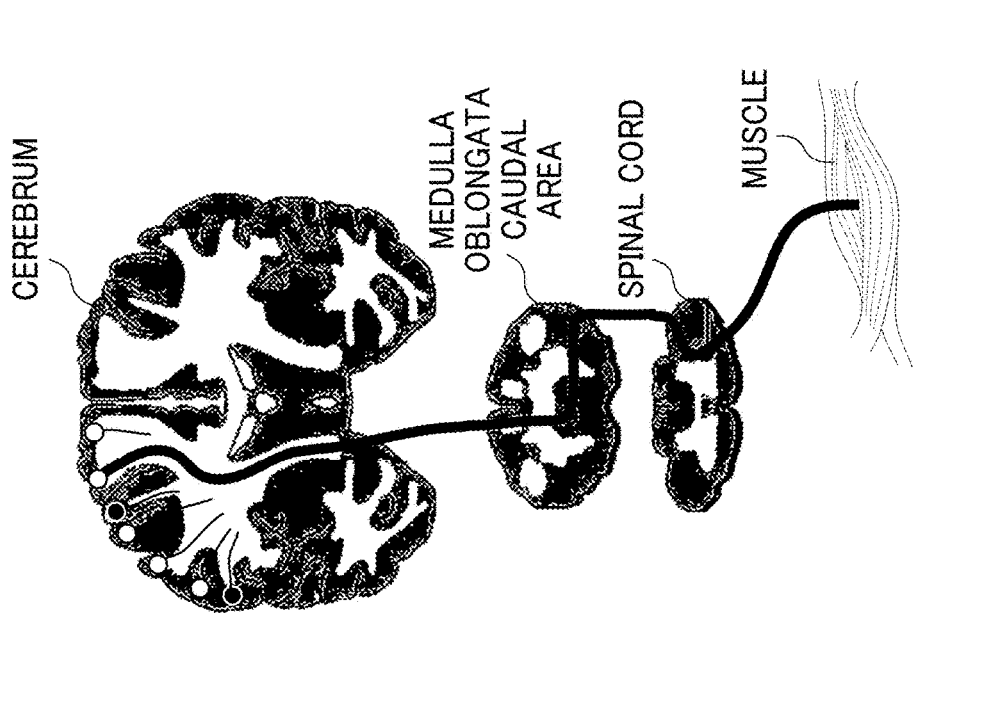
FIG. 1 is a schematic view showing a theory of rehabilitation using a BMI.
Figure 1:
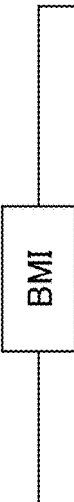

An embodiment of the present invention will be described below by referring to the drawings.

[Basic Concept of the Present Invention]

FIG. 1 is a schematic view showing a theory of rehabilitation using a BMI.

In FIG. 1, the cerebrum, the medulla oblongata caudal area, the spinal cord, and muscle associated with a brain nerve pathway are shown; each brain region in the cerebrum is indicated by a circle. It is noted that, in the circles indicating the brain regions, portions marked as black circles represent the state in which the brain region is not activated, and portions marked as white circles represent the state in which the brain region is activated.

During rehabilitation using a BMI, an activated state of a brain region (e.g., motor cortex, etc.) serving as the target is acquired; when the patient attempts movement of a hemiplegic body part, the BMI, such as a robot or a myoelectric stimulator, is actuated and assists the movement of the body part only if this brain region is activated. Then, by feeding back a kinesthetic sensation of the assisted body part to the brain, plasticity of the brain is induced. Furthermore, as a result of repeating such a process, remaining brain nerve pathways are activated and it becomes possible to move the hemiplegic body part even without the BMI.

In conventional techniques for rehabilitation using a BMI, by estimating excitability (activated state) in the somatosensory motor cortex from a scalp electroencephalogram on the opposite side (contralateral side) of the right or left paralyzed side of a body and by providing feedback according to the level thereof, recovery of function of paralyzed hand movements of stroke patients is achieved. It is noted that specific frequency components in the brain waves decrease almost simultaneously with events such as voluntary movement or stimulus, which is called event-related desynchronization (ERD), and this ERD can be used as an index of the excitability in the somatosensory motor cortex.

However, because the contralateral brain region used in the foregoing conventional technique for rehabilitation using the BMI is in the disabled side of the brain of the stroke patient, these resources are considered to be limited.

The reason that the rehabilitation is conducted using the contralateral brain region is based on the assumption that parts, such as fingers, etc., that are mainly controlled by the contralateral brain nerve pathway are assumed to be the target of the conventional rehabilitation using a BMI.

On the other hand, in order to regain motions for the daily life of hemiplegic stroke patients, it is important to recover not only motion of the fingers (such as gripping motions) but also motion of the shoulder and elbow (such as a reaching motion in which the shoulder and elbow bend and extend).

With regard to motion of the shoulder and elbow, unlike motion of the fingers, control is performed in a fixed ratio not only by a contralateral brain nerve pathway but also by an ipsilateral brain nerve pathway.

Figure 2:
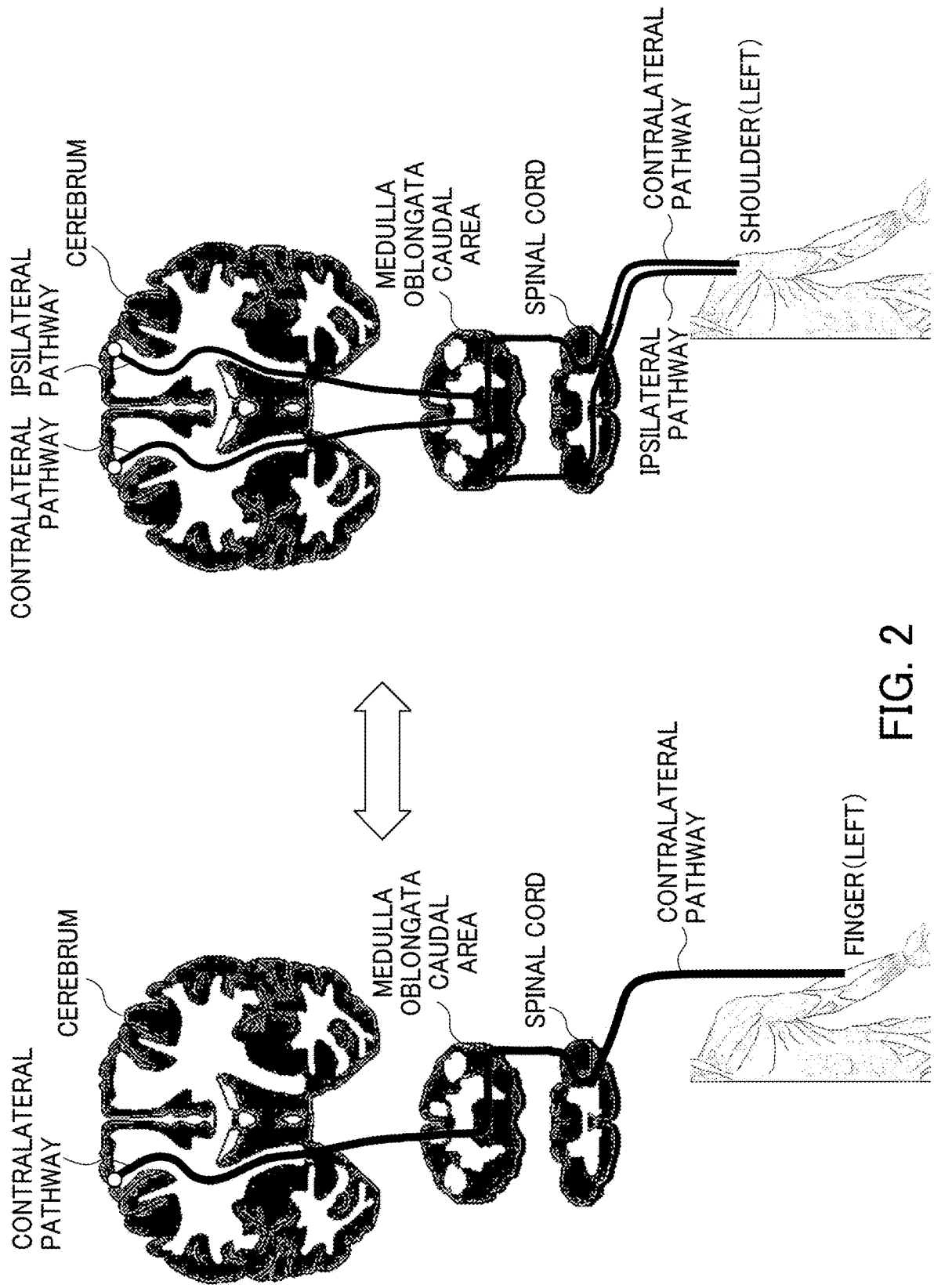
FIG. 2 is a schematic view showing a relationship between a finger and shoulder and brain nerve pathways controlling them.

FIG. 2 is a schematic view showing the relationship between the finger(s) and shoulder and brain nerve pathways controlling them.

As shown in FIG. 2, whereas the fingers are substantially controlled by a contralateral brain nerve pathway, control of the shoulder by brain nerve pathways of the contralateral side and the ipsilateral side is the same level.

Therefore, in the present invention, according to a BMI technique for switching brain information channels (brain nerve pathways used for function recovery), excitability in the somatosensory motor cortex is estimated from a scalp electroencephalogram on the ipsilateral side corresponding to the non-handicapped side of the hemiplegic patient and then feedback, such as shoulder elevation movement assistance of a paralyzed upper limb using an upper limb exoskeleton robot or electronic stimulus of an upper limb proximal muscle using an electronic stimulator, is provided in accordance with the level thereof.

In this way, in the present invention, with an increase in excitability in the ipsilateral somatosensory motor cortex, recovery of paralyzed upper limb function centered on the proximal muscle, which accompanies this, is intended. That is, by switching the brain nerve pathway used for recovering the function of the body part to a brain information channel extending from the ipsilateral somatosensory motor cortex to the paralyzed upper limb, it becomes possible to select and train an appropriate brain region that causes the body part to function.

[Configuration]

Figure 3:
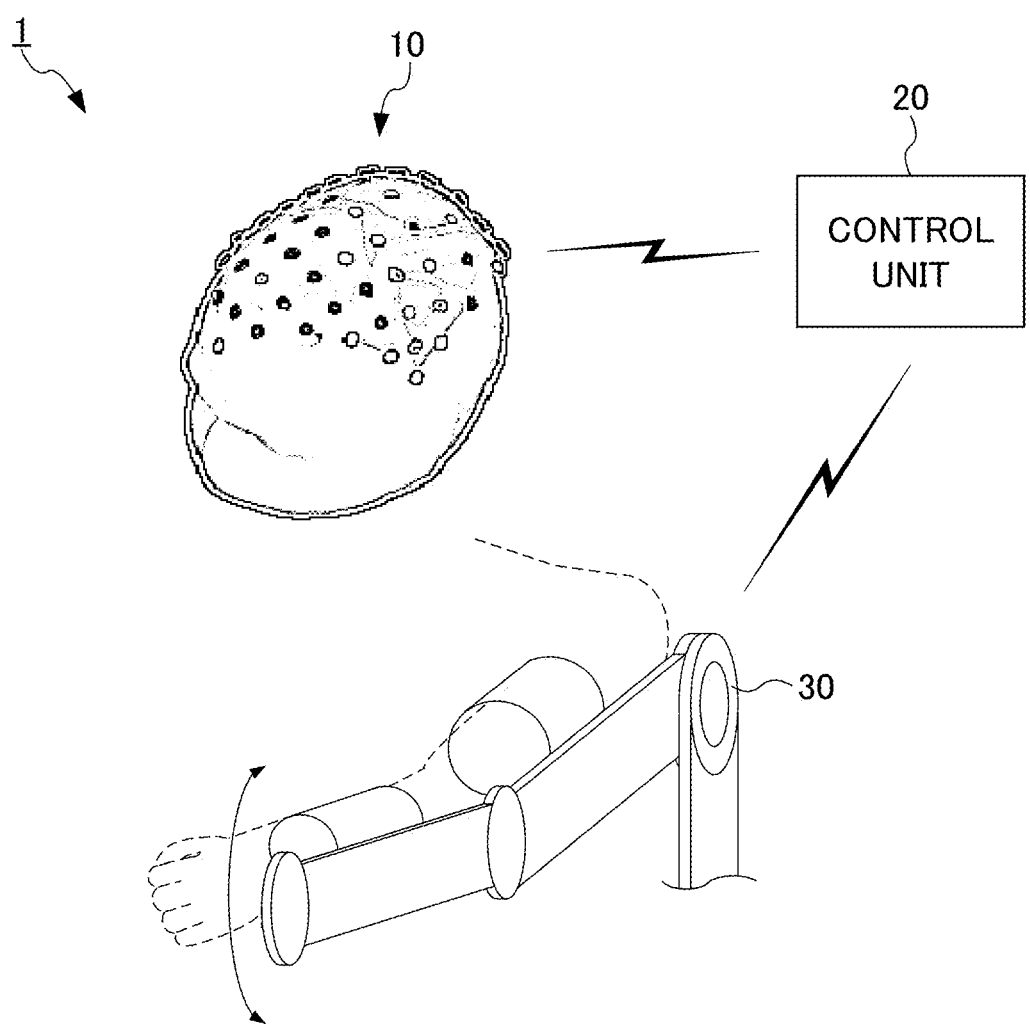
FIG. 3 is a schematic view showing an overall configuration of a biometric information processing device according to the present invention.

FIG. 3 is a schematic view showing an overall configuration of a biometric information processing device 1 according to the present invention.

The biometric information processing device 1 includes a brain wave detecting unit 10 (biometric information detecting unit), a control unit 20 (determination unit), and a movement assisting unit 30 (output unit); these units are configured to be capable of communicating with each other by wired communication or wireless communication.

The brain wave detecting unit 10 includes electrodes for detecting brain waves as biometric information of the brain based on potential changes on the scalp. In the present embodiment, the brain wave detecting unit 10 is configured as a plurality of electrodes arranged in a matrix over the entire scalp. Based on the result of the detection by the brain wave detecting unit 10, the control unit 20 can acquire activated state(s) in the brain including location(s) of an activated brain region or activated brain regions and the activation level(s) thereof. Brain wave signals detected by the brain wave detecting unit 10 are amplified to a signal level appropriate for processing in a subsequent stage and then transmitted to the control unit 20. It is noted that, in order to acquire activated states of brain regions, in addition to detecting brain waves as biometric information of the brain, blood flow rates in the brain also may be detected using a sensor that detects changes in brain blood flow using near-infrared spectroscopy.

The control unit 20 is constituted by an information processor such as a PC (personal computer), a tablet computer, a smartphone, etc. Furthermore, by executing the brain activation state determination processing described below, the control unit 20 controls the movement assisting unit 30 based on the detection result of the brain wave detecting unit 10.

Figure 4:
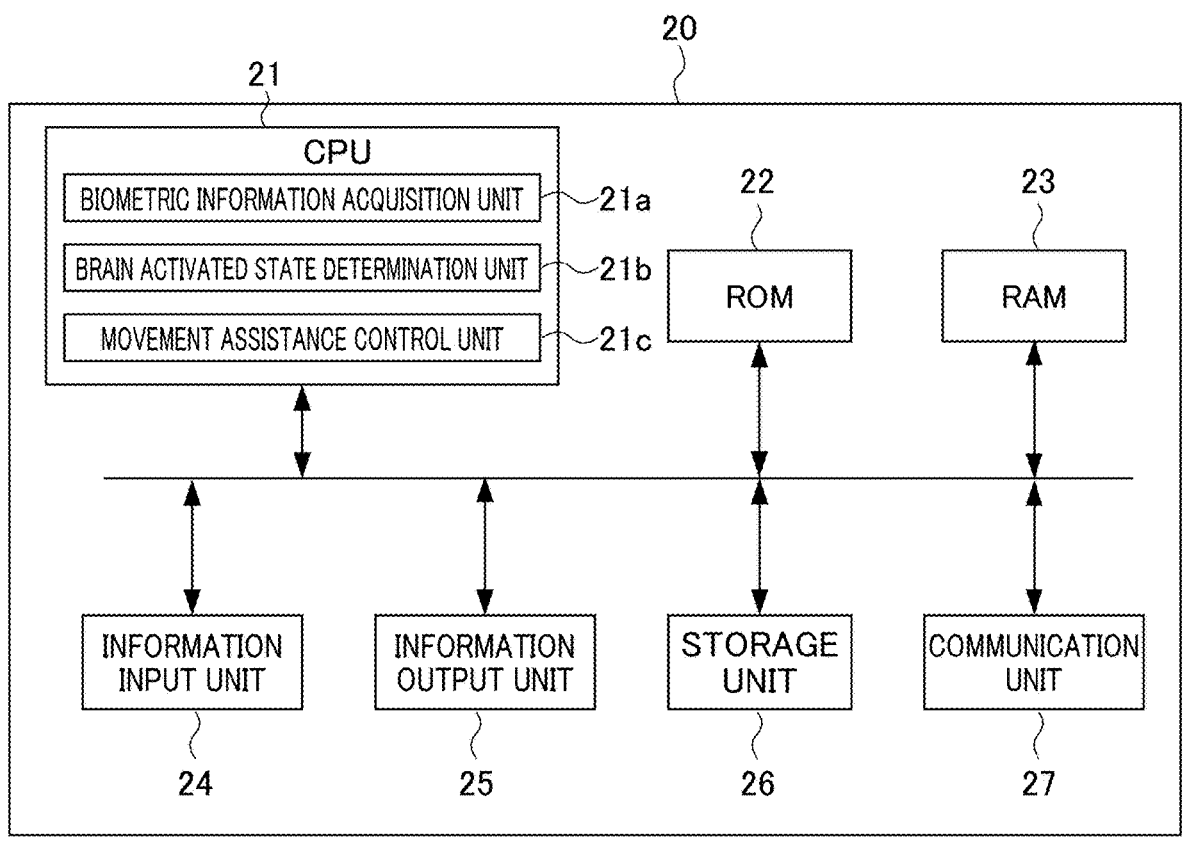
FIG. 4 is a block diagram showing the configuration of an information processor constituting a control unit.

FIG. 4 is a block diagram showing the configuration of the information processor that constitutes the control unit 20.

As shown in FIG. 4, the control unit 20 includes a CPU (central processing unit) 21, ROM (read-only memory) 22, RAM (random access memory) 23, an information input unit 24, an information output unit 25, a storage unit 26, and a communication unit 27.

The CPU 21 performs various types of processing according to programs stored in the ROM 22 or the storage unit 26.

The ROM 22 stores various types of programs for controlling the biometric information processing device 1.

The RAM 23 stores data, etc. in order for the CPU 21 to execute the various processes.

The information input unit 24 is constituted by an input device, such as a keyboard and a mouse or a touch panel, and inputs various types of information according to instruction operations of the user.

The information output unit 25 is constituted by a display or a speaker, and displays information or outputs sounds under the control of the CPU 21.

The storage unit 26 is constituted by a storage unit, such as a hard disk, and stores various types of data and various programs to be used by the biometric information processing device 1.

The communication unit 27 communicates with other devices via a wired communication using a Universal Serial Bus (USB) cable or via wireless communication such as Bluetooth®.

In a biometric information processing device 1 having such a configuration, because the CPU 21 executes a program for the brain activation state determination processing, a biometric information acquisition unit 21a, a brain activation state determination unit 21b, and a movement assistance control unit 21c are formed as functional configurations in the CPU 21.

The biometric information acquisition unit 21a acquires brain wave data from brain regions detected by the brain wave detecting unit 10 as biometric information indicating activated states in the brain. In the present embodiment, in a patient having hemiplegia in a left finger and left shoulder, it is intended that the biometric information acquisition unit 21a acquires brain waves in a brain region in the somatosensory motor cortex of the right brain and in the somatosensory motor cortex of the left brain as an example of a situation in which function of the left shoulder is the rehabilitation target. It is noted that, in this case, if at least brain waves of the brain regions of the somatosensory motor cortex of the right brain and of the somatosensory motor cortex of the left brain are acquired, it is possible to execute the brain activation state determination processing. Alternatively, brain waves of brain regions detected by all of the electrodes of the brain wave detecting unit 10 may be acquired, and the absence of activation occurring in brain regions other than the brain region(s) that is (are) the target of rehabilitation may also be determined.

Based on brain wave data of the brain regions acquired by the biometric information acquisition unit 21a, the brain activation state determination unit 21b determines whether or not the activated state(s) in the brain conform(s) to a predetermined condition for actuating the movement assisting unit 30 (hereinafter called a "movement assistance condition").

In the present embodiment, because the function of the left shoulder is a target of rehabilitation for the patient having hemiplegia in the left finger(s) and left shoulder, the brain region in the somatosensory motor cortex of the right brain is used for recovery of the function of the left finger(s), while the brain region in the somatosensory motor cortex of the ipsilateral left brain is used for recovery of the function of the left shoulder. For this reason, a decrease of specific frequency component(s) of the detected brain waves at the position of the scalp corresponding to the brain region in the somatosensory motor cortex of the left brain (that is, ERD is occurring) is set as the movement assistance condition. More specifically, when the amplitude of oscillation (mu rhythm) having a principal component of 8 to 13 Hz in the brain waves becomes smaller than a set threshold is set as the movement assistance condition. It is noted that the threshold for the amplitude of oscillation (mu rhythm) of 8 to 13 Hz in the brain waves can be set to a value corresponding to the ERD of an individual patient.

If it is determined in the brain activation state determination unit 21b that the brain wave data of the brain region(s) acquired by the biometric information acquisition unit 21a conforms to the movement assistance condition, the movement assistance control unit 21c outputs an instruction signal that causes the movement assisting unit 30 to be driven.

The movement assisting unit 30 supports a hemiplegic arm of the patient; when the driving-instructing instruction signal from the movement assistance control unit 21c is input, the movement assisting unit 30 assists the movement that lifts the hemiplegic arm of the patient using an actuator.

Figure 5:
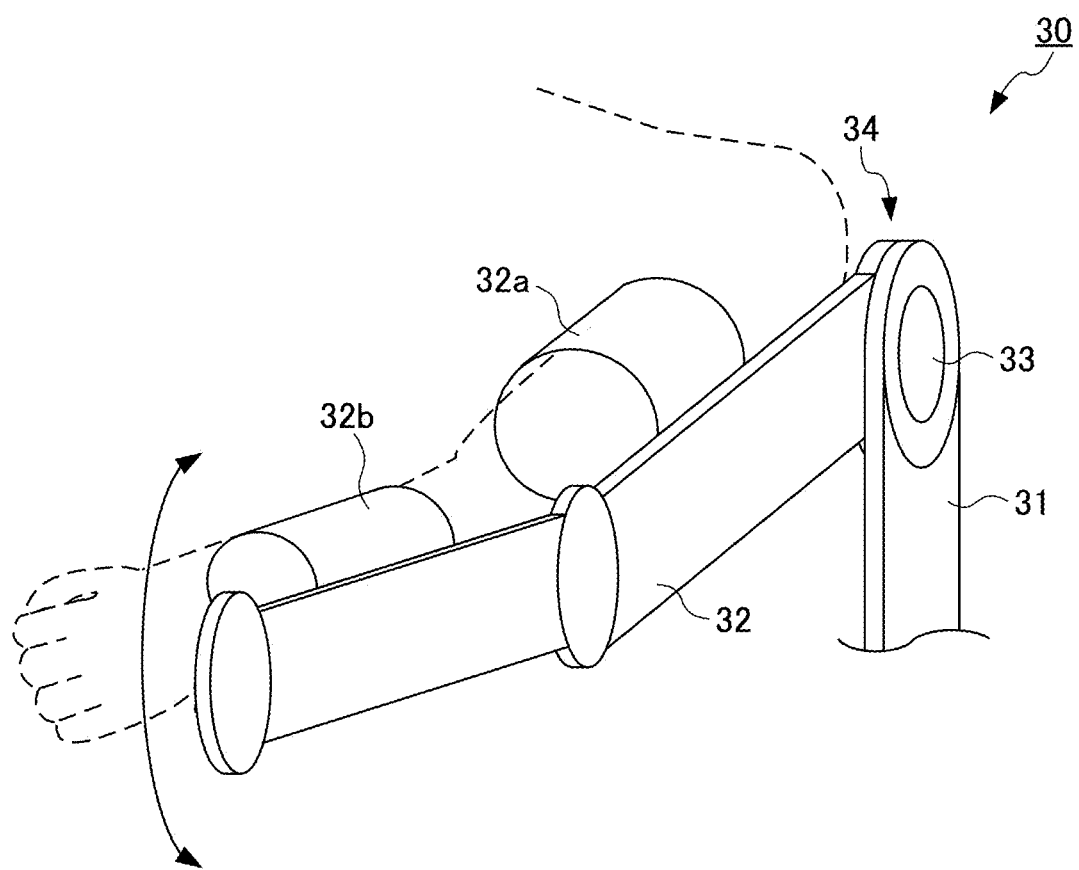
FIG. 5 is a schematic view showing the configuration of a movement assisting unit.

FIG. 5 is a schematic view showing the configuration of the movement assisting unit 30.

As shown in FIG. 5, the movement assisting unit 30 is configured as an upper limb exoskeleton robot that includes a body support part 31, an arm part 32, a coupling part 33, and an actuator 34.

The body support part 31 is fixed to a chair in which the patient sits and rotatably holds the arm part 32 via the coupling part 33. Rotational movement of the body support part 31 relative to the arm part 32 is driven by the actuator 34.

The arm part 32 is an arm member this disposed along an arm of the patient; the arm part 32 has a section corresponding to the upper arm and a section corresponding to the forearm of the patient; these sections are continuous with each other and are bent at a predetermined angle (an angle at which the patient slightly bends his or her elbow). The upper end of the section of the arm part 32 corresponding to the upper arm is coupled by the coupling part 33 so as to be rotatable relative to the body support part 31 in the vertical direction. In addition, the section corresponding to the upper arm and the section corresponding to the forearm of the arm part 32 are provided with a belt member 32a and a belt member 32b, respectively, for supporting the upper arm and the forearm of the patient.

The coupling part 33 couples the arm part 32 with respect to the body support part 31 so that it is rotatable in the vertical direction.

The actuator 34 outputs a driving force for causing the arm part 32 to rotate relative to the body support part 31.

The biometric information processing device 1 having such a configuration detects brain waves of a patient who is attempting to elevate the left shoulder and determines whether or not a brain region (here, an ipsilateral brain region) that is a target of the rehabilitation is activated.

Figure 6:
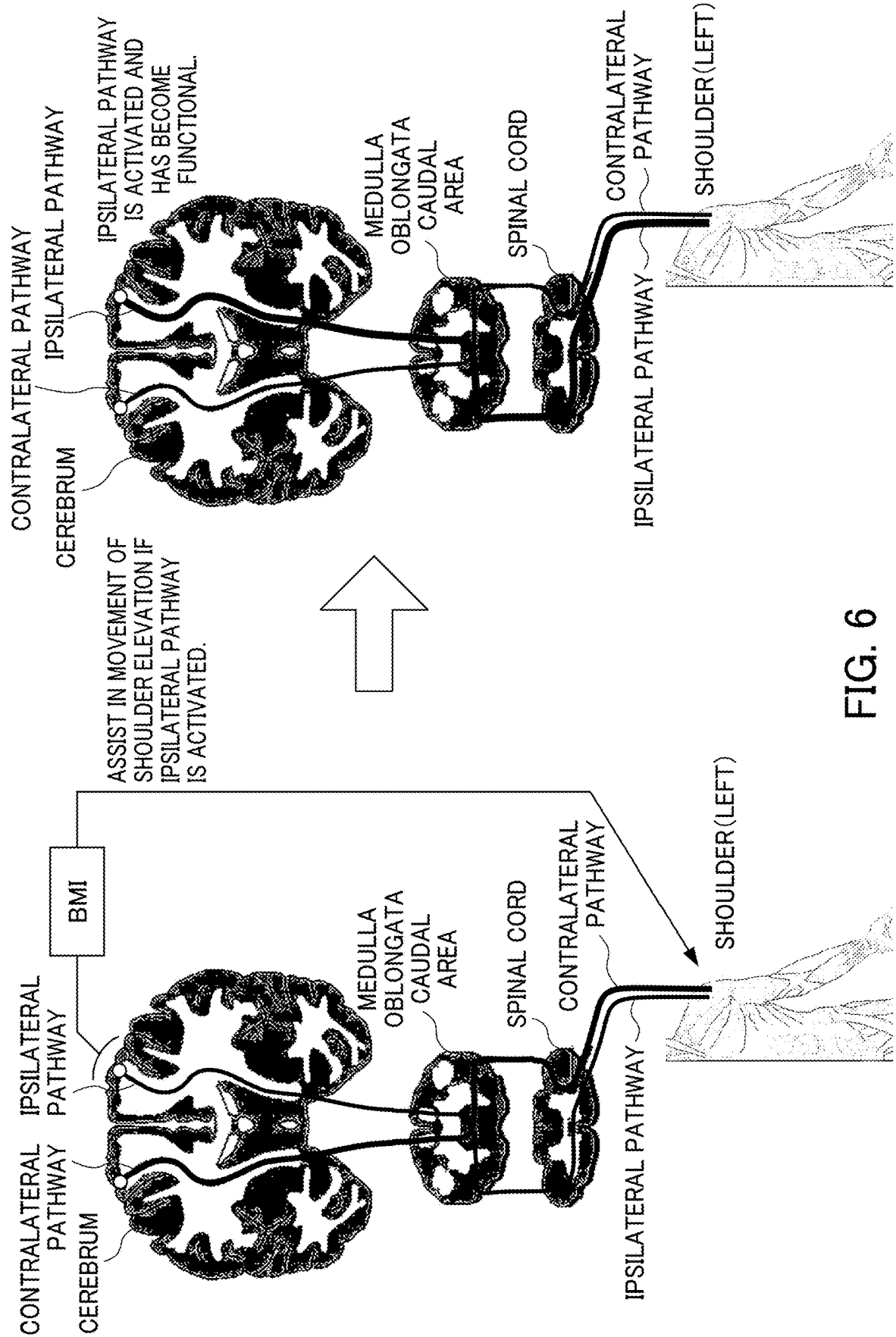
FIG. 6 is a schematic view showing a state in which, while a patient attempts to elevate the left shoulder, an ipsilateral brain region of the patient is activated.

FIG. 6 is a schematic view showing the state in which, while the patient attempts to elevate the left shoulder, an ipsilateral brain region of the patient is activated.

If the patient attempts a specific motion such as elevation of the left shoulder, any brain region connected via a brain nerve pathway to the body part that performs the motion is activated. In the present embodiment, as described above, a brain nerve pathway to be used for the specific motion (here, elevation of the left shoulder) is selected; when the patient attempts the specific motion, training is performed by the biometric information processing device 1 to activate a brain region connected to the selected brain nerve pathway (ipsilateral brain nerve pathway).

That is, when the patient attempts a specific motion using a hemiplegic body part and it is determined that a specific brain region has been activated, movement assistance is performed by the movement assisting unit 30 in the biometric information processing device 1. Then, by feeding back a kinesthetic sensation of the assisted body part to the brain, plasticity of the brain is induced. By repeating this, initially, from a state in which there are variations in the brain regions that active when a specific motion is attempted, the targeted brain region(s) is (are) gradually trained to achieve an activated state and it becomes possible to move the hemiplegic body part using the patient's own brain nerve pathways even without the assistance of the movement assisting unit 30.

Figure 7:
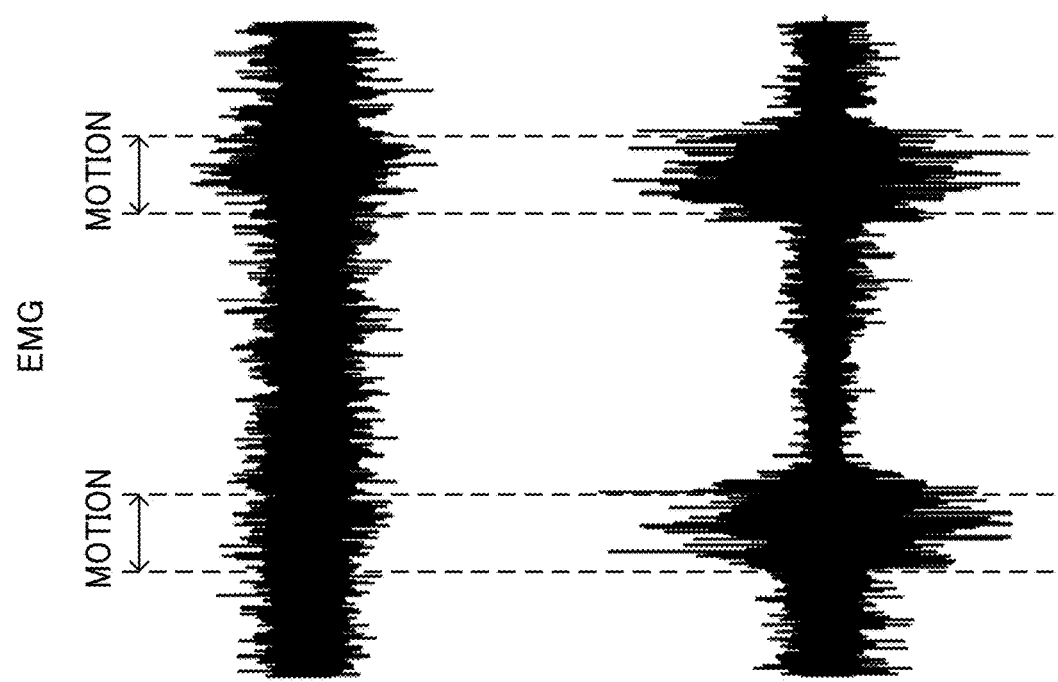
FIG. 7 is a schematic view showing an example of how a specific brain region is activated by training.
Figure 7:
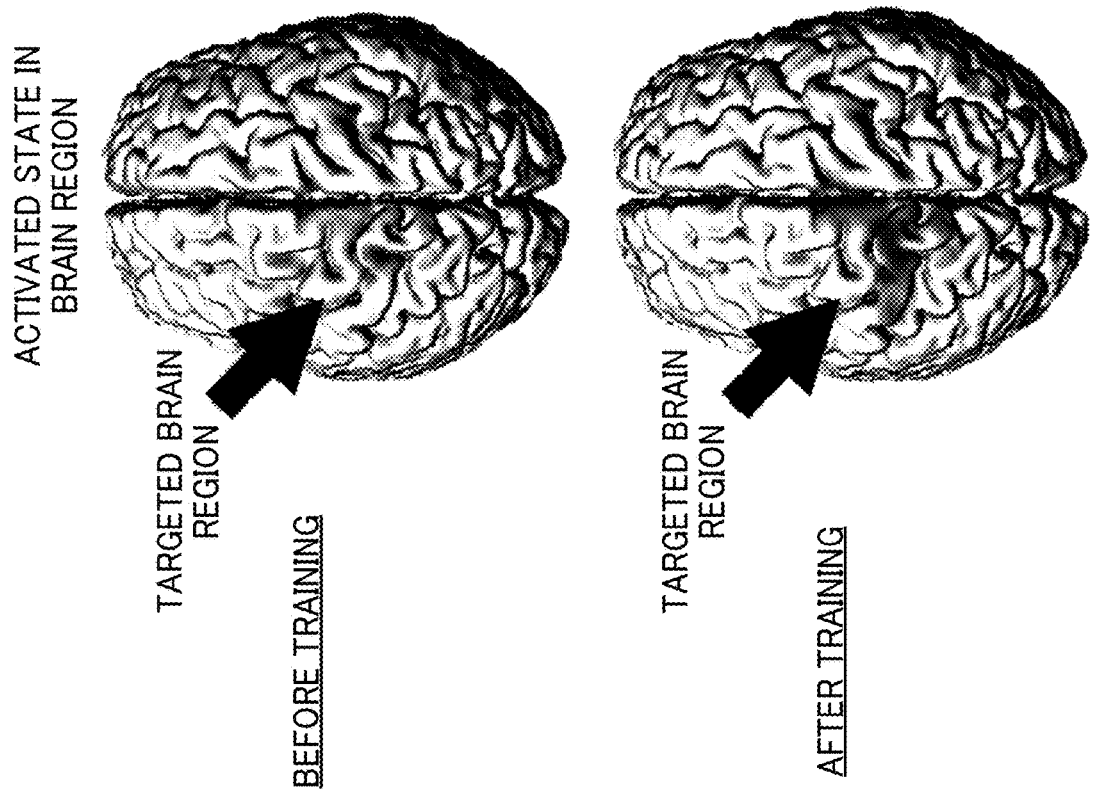

FIG. 7 is a schematic view showing an example of how a specific brain region is activated by training. It is noted that, in FIG. 7, schematic views of a brain showing an activated state in a brain region, and electromyograms (EMG) of the body part (paralyzed muscle) controlled by this brain region, are shown.

In the schematic view of the brain of FIG. 7, by indicating the brain region that is being activated (ERD has occurred) using a portion of higher density, it is understood that the function of the paralyzed muscle is recovered by activating the brain region associated with the specific motion by training.

[Operation]

The operation of the biometric information processing device 1 will be described next.

Figure 8:
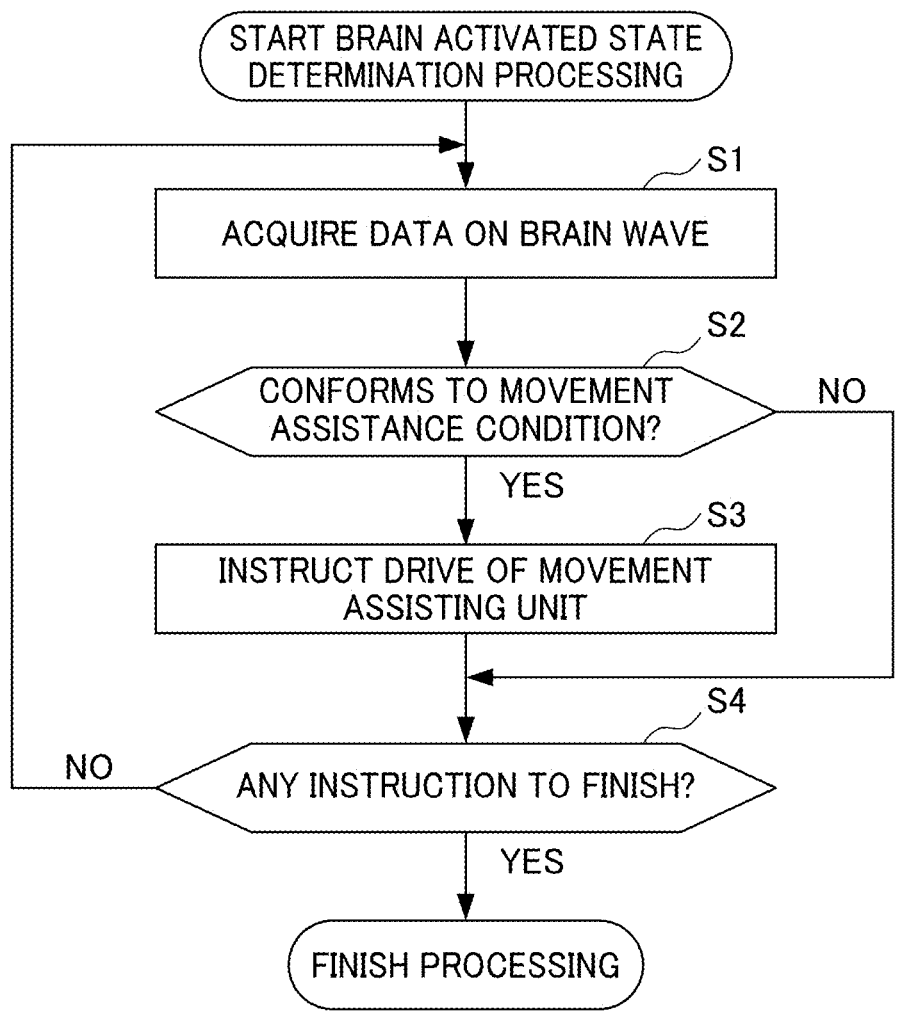
FIG. 8 is a flowchart showing the flow of a brain activation state determination processing.

FIG. 8 is a flowchart showing the flow of the brain activation state determination processing.

The brain activation state determination processing is started by inputting, via the information input unit 24, an instruction to perform the brain activation state determination processing.

In step S1, the biometric information acquisition unit 21a acquires brain wave data of brain regions detected by the brain wave detecting unit 10 as biometric information indicating an activated state or activated states in the brain.

In step S2, based on the brain wave data of the brain regions acquired by the biometric information acquisition unit 21a, the brain activation state determination unit 21b determines whether or not the activated state(s) in the brain conform(s) to a predetermined condition for actuating the movement assisting unit 30 (movement assistance condition).

If the activated state(s) in the brain do(es) not conform to the movement assistance condition, then a determination NO is made in step S2, and the processing proceeds to step S4.

On the other hand, if the activated state(s) in the brain conform(s) to the movement assistance condition, then a determination YES is made in step S2, and the processing proceeds to step S3.

In step S3, the movement assistance control unit 21c outputs an instruction signal that causes the movement assisting unit 30 to be driven. In response to this, the actuator 34 of the movement assisting unit 30 outputs a driving force for causing the arm part 32 to rotate relative to the body support part 31. That is, the arm part 32 of the movement assisting unit 30 is rotated upward relative to the body support part 31 to assist the patient in the movement that elevates the left shoulder.

In step S4, the brain activation state determination unit 21b determines whether or not an instruction to terminate the brain activation state determination processing has been input.

If an instruction to terminate the brain activation state determination processing has not been input, a determination NO is made in step S4, and the processing proceeds to step S1.

On the other hand, if an instruction to terminate the brain activation state determination processing has been input, a determination YES is made in step S4, and the brain activation state determination processing terminates.

Effects of the Embodiment

Figure 9:
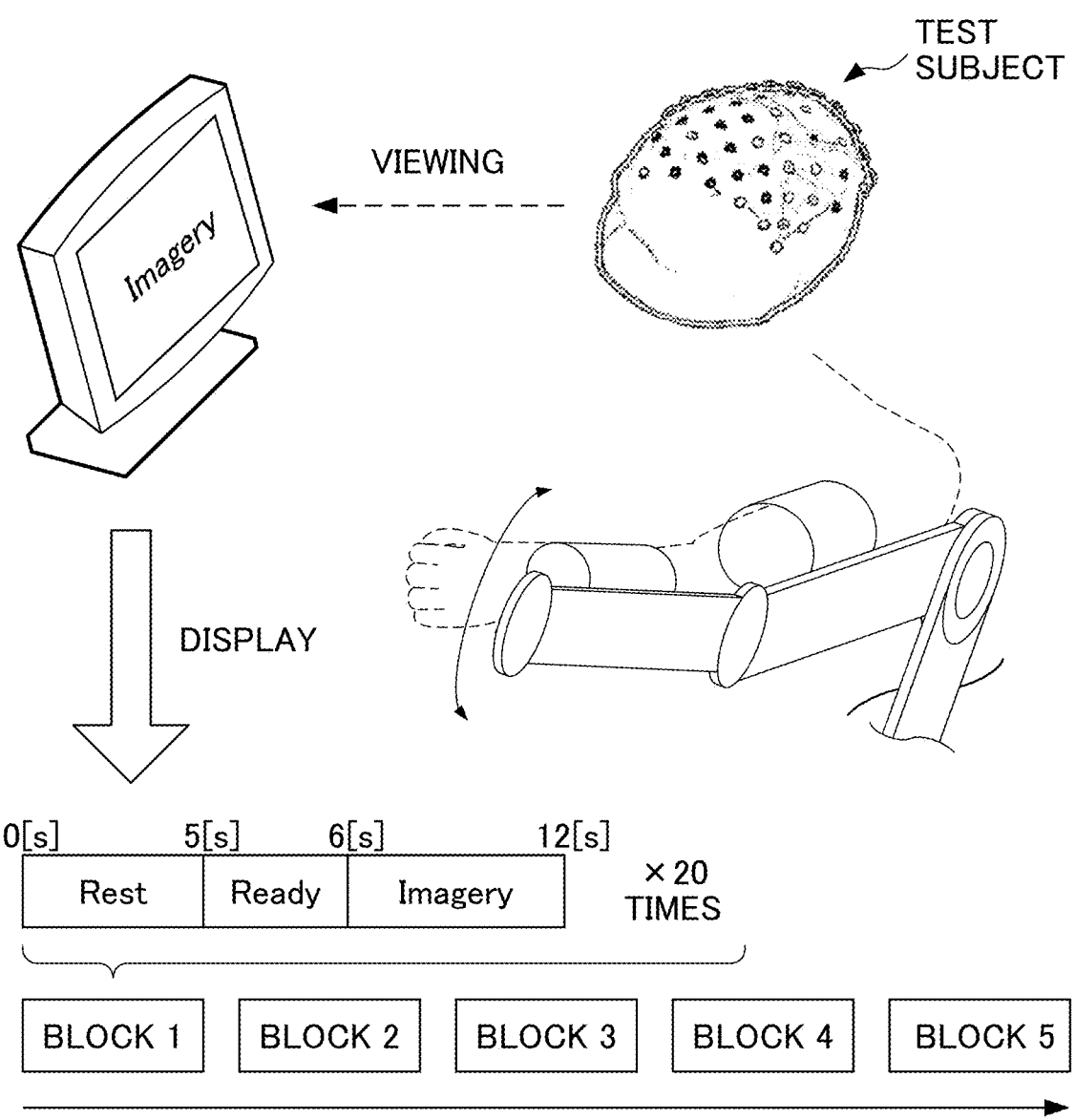
FIG. 9 is a diagram showing a specific example of shoulder elevation BMI training on a hemiplegic stroke patient using ERD on the ipsilateral side (non-handicapped side).

FIG. 9 is a view showing a specific example of shoulder elevation BMI training of a hemiplegic stroke patient using ERD on the ipsilateral side (non-handicapped side).

In the example shown in FIG. 9, by employing an electrode arrangement based on the international 10-20 method, ERD of brain waves detected by electrodes at the C3 (left brain) position and the C4 (right brain) position were used as biomarkers for shoulder elevation movement in accordance with brain activity of the ipsilateral side.

Then, when the test subjects (a patient and a non-handicapped person) attempted to elevate the shoulder corresponding to the paralyzed side, the attached upper limb exoskeleton robot passively elevated the shoulder when the ipsilateral ERD exceeded a prescribed threshold.

In this example, by performing a total 100 of repetitive trainings in five blocks of twenty times in each day of training, training of paralyzed upper limb movement of hemiplegic patients was performed.

Furthermore, by conducting shoulder elevation BMI training in a single day on three non-handicapped persons and four hemiplegic patients and by conducting shoulder elevation BMI training for three consecutive days on one non-handicapped person and one hemiplegic patient, experimental results were obtained.

It is noted that a high density electroencephalograph (128 ch, EGI, Inc.) was used as the brain wave measurement device.

With the exoskeleton robot attached, the test subject viewed a screen that displayed the characters Rest (five seconds), Ready (one second), and Imagery (six seconds) in that sequence. When Imagery was displayed, an "imagery causing the shoulder to be bent 90 degrees with elbow extension" was imagined. When the ERD of the somatosensory motor cortex on the ipsilateral (non-handicapped) side during this movement imagining became 30% or more, the upper limb exoskeleton robot passively bent the upper limb of the test subject. This was performed 20 times×five blocks per each session.

As a result, in this example, the success rate of shoulder elevation movement imagining accompanied by ipsilateral ERD exceeding the prescribed threshold in a single day of shoulder elevation BMI training was 56%±4% for the non-handicapped persons and 79%±21% for the hemiplegic patients; thus, shoulder elevation BMI training using the ipsilateral ERD was practicable in all cases.

FIG. 10 is a view showing changes in brain waves of one non-handicapped person before and after shoulder elevation BMI training was conducted on three consecutive days.

In FIG. 10, ERD average values of each channel of all recorded brain waves are indicated by shading; the higher the density, the stronger the ERD, thereby indicating that excitability (activated state) in the brain activity is increasing. When the first day and the third day are compared, a trend of increasing ipsilateral ERD during shoulder elevation imagining owing to the shoulder elevation BMI training was observed.

FIG. 11 is a view showing changes in brain waves of one hemiplegic patient before and after shoulder elevation BMI training was conducted on three consecutive days.

On the first day of the training, because a significant muscle tone increase was recognized in paralyzed deltoid muscle front fibers during the movement imagining and influence by the muscle activity was introduced into the brain waves as noise, it was excluded from the analyzed results.

For this reason, in FIG. 11 brain waves (activated states in the brain) are shown for the second day and the third day wherein resting of the paralyzed deltoid muscle front fibers was ensured during the movement imagining. The schematic views of the brain on the left side of FIG. 11 show the ERD average values. In the schematic views of the brain on the right side of FIG. 11, T-values of each channel (electrode), which were obtained by conducting a T-test using the ERD value during resting in comparison to the ERD value during the movement imagining, are shown. In the schematic views of the right side of the brain in FIG. 11, because the higher the density, the smaller the variation of ERD values of each implementation, it indicates that ERD occurs more reliably. In this way, the ipsilateral ERD average value and the T-value of the ipsilateral ERD showed an increasing trend by conducting shoulder elevation BMI training on hemiplegic patients.

FIG. 12 is a graph showing the results of clinical indicators before and after shoulder elevation BMI training was conducted for three consecutive days on one hemiplegic patient.

In this regard, the Fugl-Meyer Assessment (FMA) and Stroke Impairment Assessment Set (SIAS) are clinical assessments for a paralyzed upper limb function; the Modified Ashworth Scale (MAS) is a clinical measure for evaluating the degree of muscle tone in a paralyzed upper limb. The minimal clinically important difference (MCID) of FMA is known to be 4.25 to 7.25 points.

As shown in FIG. 12, improvement of FMA was observed in the upper limb paralysis of the hemiplegic patient by conducting shoulder elevation BMI training for three days; improvements were also observed in the shoulder elevation angle during positive movement and passive movement.

FIGS. 13 to 18 are views showing the results of BMI training conducted one hour per day for seven days on a total of five stroke patients having severe hemiplegia. It is noted that the configuration of the BMI rehabilitation system was the same as in FIG. 9.

Figure 13:
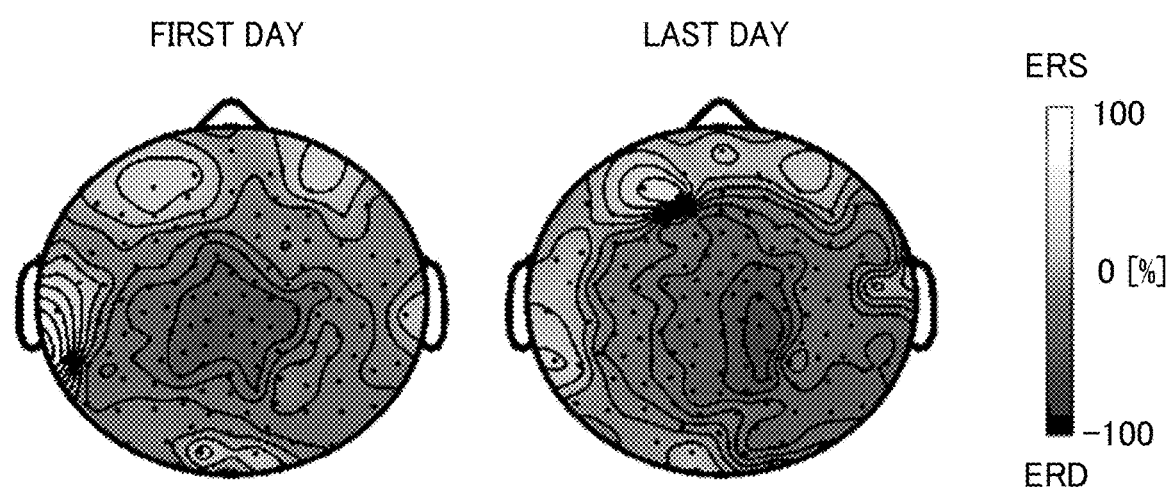
FIG. 13 is a diagram showing changes in brain waves for one representative test subject from among five stroke patients with severe hemiplegia before and after shoulder elevation BMI training was conducted for seven consecutive days.

More specifically, FIG. 13 is a diagram showing changes in brain waves of one representative test subject from among the five stroke patients having severe hemiplegia before and after shoulder elevation BMI training was conducted for seven consecutive days. In FIG. 13, the higher the density, the greater the ERD, whereas the lower the density, the greater the event-related synchronization (ERS) are shown. In addition, FIG. 14 is a diagram showing changes in the laterality index for the representative test subject of FIG. 13 before and after the shoulder elevation BMI training was conducted for seven consecutive days.

Figure 14:
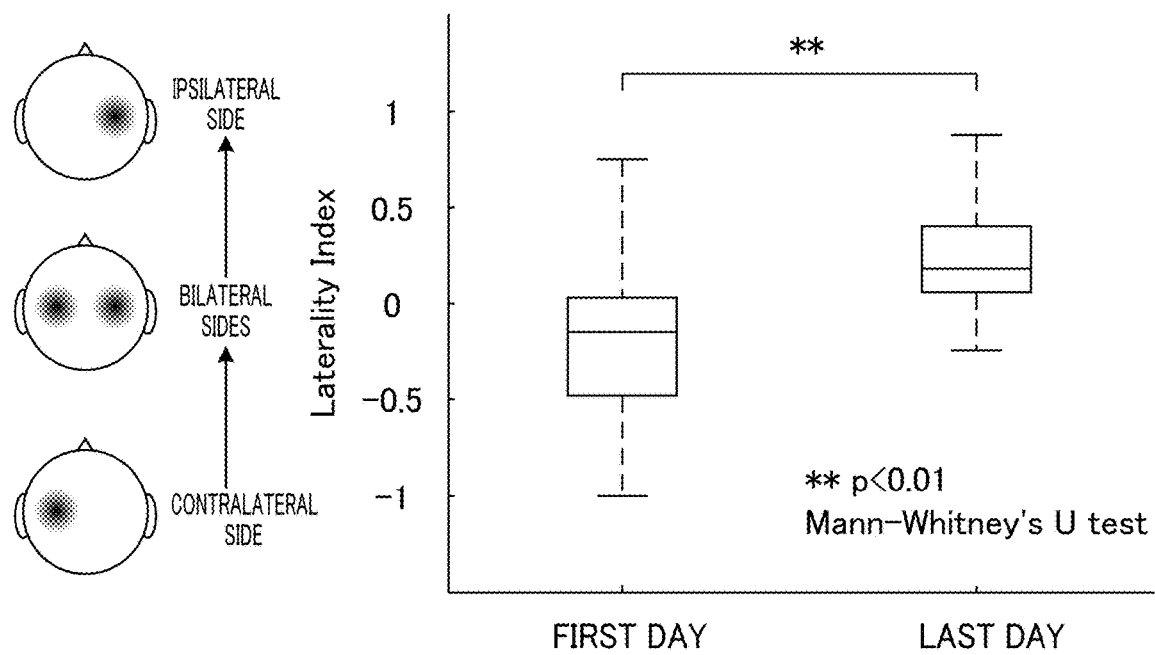
FIG. 14 is a diagram showing changes in a laterality index for the representative test subject of FIG. 13 before and after shoulder elevation BMI training was conducted for seven consecutive days.

The laterality index in FIG. 14 is defined as follows:

laterality index=(contralateral ERD−ipsilateral ERD)/
(κcontralateral ERD|+|ipsilateral ERD|).

In the BMI training shown in FIGS. 13 to 18, it was intended to detect brain waves by affixing electrodes near the motor cortex of the right hemisphere, from among the motor cortex of the left hemisphere and the motor cortex of the right hemisphere that is connected to the paralyzed right shoulder muscle, and to train the function of a nerve pathway (a pathway ipsilateral to a paralyzed limb) extending downward from the motor cortex of the right hemisphere to the shoulder muscle.

As a result, movement-related brain waves (areas of high density in FIG. 13), which were generated when the shoulder elevation movement was being planned, transitioned to the right side, which are the brain waves that are used in the training with the BMI. Based on this result, the BMI according to the present embodiment, which is intended to achieve pathway-selective function activation, is considered to have achieved the objective of selectively activating a nerve pathway extending downward from the motor cortex of the right hemisphere to the shoulder muscle.

It is noted that similar significant changes in brain waves were also confirmed in two out of the five test subjects.

Figure 15:
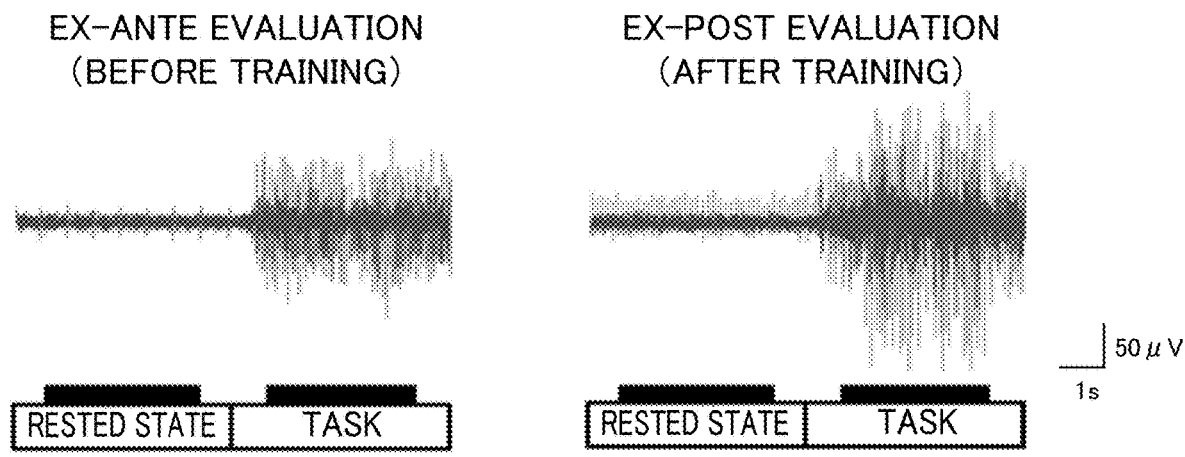
FIG. 15 is a diagram showing changes in a voluntary electromyogram of the front portion of a deltoid muscle for the representative test subject of FIG. 13.
Figure 16:
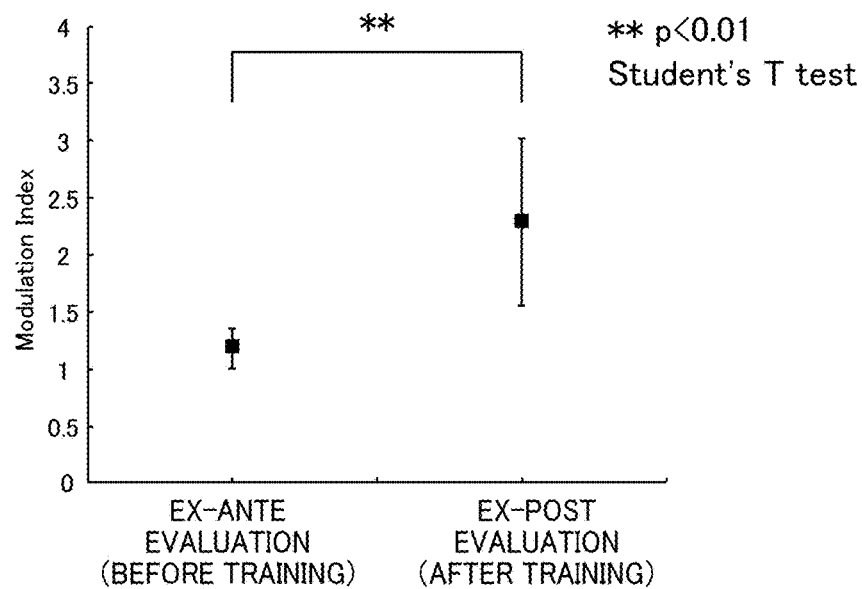
FIG. 16 is a graph showing changes in a modulation index (MI) in an electromyogram of the front portion of the deltoid muscle.

Furthermore, FIG. 15 is a view showing changes in a voluntary electromyogram of the front portion of the deltoid muscle in the representative test subject of FIG. 13. FIG. 16 is a view showing changes in the modulation index (MI) of the electromyogram of the front portion of the deltoid muscle.

The modulation index MI(t) in FIG. 16 is defined as follows:

$$MI(t)=(1/T_{task})\Sigma EMG(t)_{task}/(1/T_{rest})\Sigma EMG(t)_{rest}.$$

Here, $T_{task}$ is the number of data samples during the motion imagery, $T_{rest}$ is the number of data samples in the resting state, $EMG(t)_{task}$ is the waveform of the electromyogram during the motion imagery (during the task), and $EMG(t)_{rest}$ is the waveform of the electromyogram in the resting state.

As shown in FIGS. 15 and 16, when observing the electromyograms of the front portion of the deltoid muscle that activates during elevation of the shoulder of the paralyzed limb, the amount of this activation increased significantly after the training. This means that, as a result of selectively activating a nerve pathway extending downward from the motor cortex of the right hemisphere to the shoulder muscle as intended by using the BMI according to this embodiment, voluntary control of a muscle can be exerted more strongly.

It is noted that similar significant changes in electromyograms were also confirmed in four out of the five test subjects.

Figure 17:
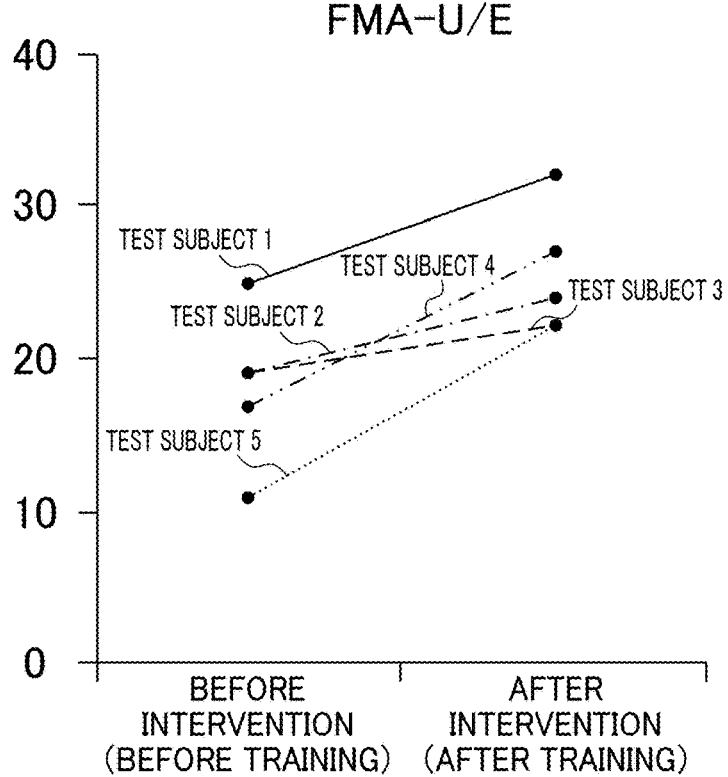
FIG. 17 is a graph showing changes in FMA-U/E (FMA upper limb item score) for five test subjects.

In addition, FIG. 17 is a view showing changes in FMA-U/E (FMA upper limb item score) among the five test subjects.

As shown in FIG. 17, when the clinical therapeutic effects achieved as a result of the foregoing BMI training were evaluated using FMA-U/E as a clinical movement evaluation index, significant function recoveries were observed in all cases.

Figure 18:
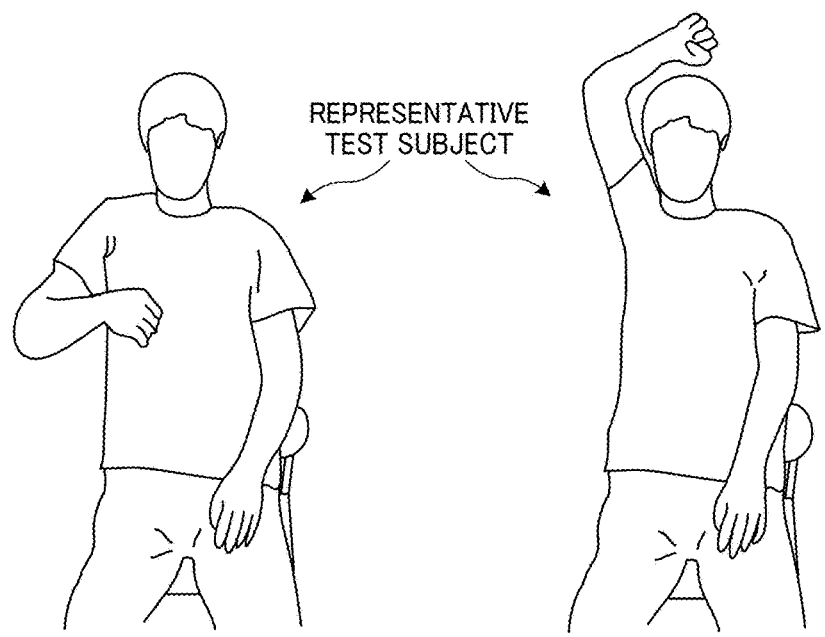
FIG. 18 is a schematic view showing a change in the function of a shoulder of a paralyzed limb for a representative test subject before and after training.

FIG. 18 is a schematic view showing a change in the function of the shoulder of the paralyzed limb of a representative test subject before and after training.

As shown in FIG. 18, as a result of having performed the foregoing BMI training, the paralyzed shoulder is brought to a state of being capable of elevating to a clearly higher position than the position before the training.

As described above, increased excitability in the ipsilateral somatosensory motor cortex during the shoulder elevation movement imagining in non-handicapped persons and hemiplegic patients, and the resultant effect of recovering the function of a paralyzed upper limb in hemiplegic patients were observed as characteristic effects produced by the present invention. This is considered to be phenomena brought about in accordance with switching of the brain information channel (brain nerve pathway) that extends from the ipsilateral somatosensory motor cortex to the paralyzed upper limb.

[First Modification]

In the foregoing embodiment, before the execution of the brain activation state determination processing, processing (brain region selection processing) can be performed in which a trend in the activated state(s) of brain region(s) in the same patient is (are) detected, and based on the result of the detection, a brain region is selected to become the target of rehabilitation.

Figure 19:
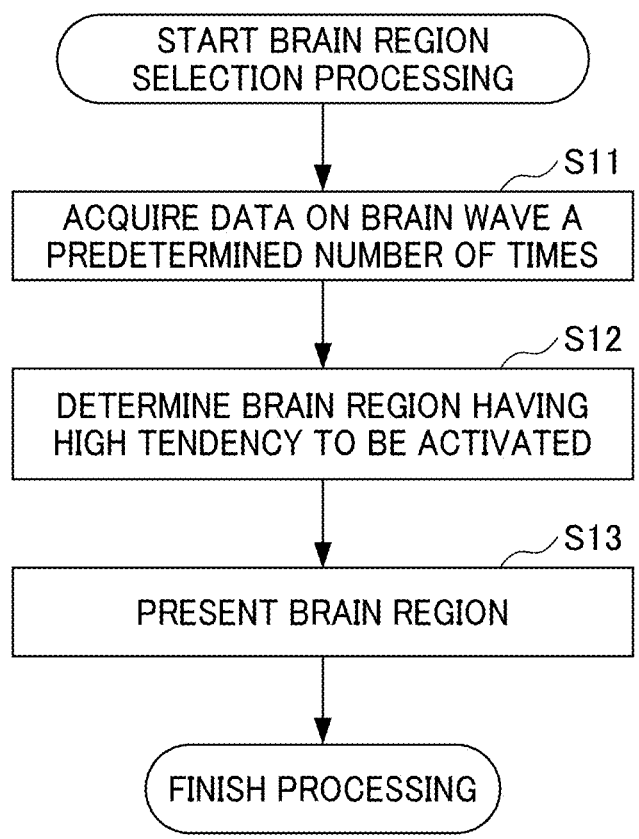
FIG. 19 is a flowchart showing the flow of a brain region selection processing.

FIG. 19 is a flowchart showing the flow of the brain region selection processing.

The brain region selection processing is started by inputting, via the information input unit 24, an instruction to execute the brain region selection processing.

In step S11, the biometric information acquisition unit 21a repeats the process of acquiring brain waves from each brain region of a patient who is performing a specific motion using a hemiplegic body part a predetermined number of times. For example, in step S11, the patient repeats the specific motion five times using the hemiplegic body part, and the biometric information acquisition unit 21a acquires brain waves from each brain region corresponding to the motion performed five times.

In step S12, the brain activation state determination unit 21b determines a brain region having a high tendency to be activated by the specific motion using the hemiplegic body part.

In step S13, the brain activation state determination unit 21b presents the brain region (presentation on a display, etc.) that was determined to have a high tendency to be activated by the specific motion using the hemiplegic body part as a brain region suitable to be a target of the rehabilitation.

At this time, a suitable brain region from among previously designated brain regions (e.g., brain regions limited to the ipsilateral side or selected brain regions not highly activated at the present time but determined to have a high tendency to be activated by training) may be presented as the target.

By performing the brain region selection processing before the execution of the brain activation state determination processing and training, it is possible to recover the body function more efficiently by selecting a brain region of the patient that is suitably activated in accordance with the specific motion that will be performed in the training.

[Second Modification]

In the brain activation state determination processing in the foregoing embodiment, if an activated state of the brain conforms to the movement assistance condition, it was intended to assist the patient in the movement that elevates the left shoulder using the movement assisting unit 30.

In contrast thereto, instead of performing the movement assistance using the movement assisting unit 30, when the activated state(s) in the brain conform(s) to the movement assistance condition, an indication may be displayed on a display showing that the activated state(s) in the brain is (are) adequate.

By doing this, it is possible to easily perform the training without using the movement assisting unit 30. That is, the patient can perform the rehabilitation at home, etc.

It is noted that, in addition to performing movement assistance using the movement assisting unit 30, an indication may be displayed on the display showing that the activated state(s) in the brain is (are) adequate.

[Third Modification]

In the foregoing embodiment, if an activated state in the brain does not conform to the movement assistance condition, a perceptual stimulus (such as pain, vibration, compression, electronic stimulus, or sound) notifying that the activated state of the brain is not appropriate may be given to the patient.

By giving such a stimulus, it is possible to increase the retention rate of the training effect in the patient.

It is noted that the present invention is not limited to the foregoing embodiments; modifications, improvements, etc. can be added to the present invention appropriately within a range in which the effects of the present invention are achieved.

For example, in the foregoing embodiment, in addition to a brain region ipsilateral to the hemiplegic body part, a brain region may be selected from among a plurality of selectable contralateral brain regions and may be trained. In addition, a brain region contralateral to the hemiplegic body part and an ipsilateral brain region may be selected, and a plurality of brain regions may be trained as brain regions that are the targets of the rehabilitation.

In the case of adults, movement-related regions, such as a somatosensory motor cortex, a supplementary motor area, a premotor cortex, a presupplementary motor area, etc., can be the brain regions selected at this time. On the other hand, in the case of children or infants, the selected brain regions can include brain regions such as a sensory area other than movement-related regions, in addition to the movement-related regions.

The brain region(s) to be selected from these brain regions is (are) suitably determined in consideration of the condition of each patient such as the severity of a stroke, the size of the damaged tissue or the damaged site, whether the stroke occurred during childhood, the presence of brachial plexus palsy (avulsion syndrome), the presence of spinal cord injury, the presence of cerebral palsy, the presence of neuromuscular intractable disease, etc.

In addition, in the foregoing embodiment, although cases were described in which function recovery of a hemiplegic body part of patients is performed, it is not limited to this. That is, training may be performed using the biometric information processing device 1 to improve the function of body parts of non-handicapped persons.

In addition, in the foregoing embodiment, although the brain wave detecting unit 10 is constituted by electrodes arranged in a matrix over the entire scalp, it is not limited to this. That is, it may be formed by providing one electrode or multiple electrodes at a position or positions on the scalp corresponding to the brain region(s) selected as the target(s) of the rehabilitation.

In addition, in the foregoing embodiment, although a case was described in which the movement assisting unit 30 is configured as an upper limb exoskeleton robot, it is not limited to this. That is, as long as it can assist the movement of the patient, a device having a different configuration is applicable; for example, it can be configured as an electronic stimulator that applies myoelectric stimulus to a hemiplegic body part.

In addition, it is possible to practice the present invention by combining the foregoing embodiment and each of the foregoing modifications.

It is possible to perform the processing in the foregoing embodiment either by hardware or by software.

That is, as long as the biometric information processing device 1 is provided with a function capable of executing the foregoing processing, the functional configuration and the hardware configuration for realizing this function are not limited to those described in the foregoing examples.

If the foregoing processing is executed by software, a program constituting this software is installed on a computer from a network or a storage medium.

The storage medium storing the program is constituted as a removable medium to be distributed and is separate from a device body, as a storage medium incorporated in advance in the device body, etc. The removable medium is constituted as a magnetic disk, an optical disk, a magneto-optical disk, etc. The optical disk is constituted as a compact disk read-only memory (CD-ROM), a digital versatile disk (DVD), a Blu-ray® Disk, etc. The magneto-optical disk is constituted as a mini-disk (MD), etc. The storage medium incorporated in advance in the device body is constituted as a ROM, a hard disk storing a program, etc.

A biometric information processing device 1 having such a configuration includes the brain wave detecting unit 10, the control unit 20, and the movement assisting unit 30.

The brain wave detecting unit 10 detects biometric information from at least one brain region from among a plurality of brain regions that are selectable in accordance with the body part that is to become a target of function recovery or function improvement.

The control unit 20 determines, based on the biometric information from the brain region(s) detected by the brain wave detecting unit 10, an activated state in the brain including location(s) of the brain region(s) that is (are) activated in a test subject attempting movement of said body part and the activation level of said brain region(s).

The movement assisting unit 30 performs a predetermined motion when it is determined by the control unit 20 that the activated state(s) in the brain conform(s) to a predetermined condition.

As a result, it is possible to perform training by selecting an appropriate brain region, which causes the body part to function, from among multiple brain regions that are selectable for the body part to become the target(s) of function recovery or function improvement.

The brain wave detecting unit 10 detects biometric information in a brain region ipsilateral to the body part that is to become a target of function recovery or function improvement.

As a result, it is possible to perform training that causes the body part to function by using a brain region selected from brain regions ipsilateral to the body part.

The brain wave detecting unit 10 detects biometric information in a brain region contralateral to the body part that is to become a target of function recovery or function improvement.

As a result, it is possible to perform training that causes the body part to function by using a brain region selected from brain regions contralateral to the body part.

The brain wave detecting unit 10 detects biometric information in a brain region ipsilateral to a first body part that is to become a target of function recovery or function improvement and detects biometric information in a brain region contralateral to a second body part that is to become a target of function recovery or function improvement.

As a result, it is possible to perform training that causes multiple body parts to function by using a brain region or brain regions selected from brain regions contralateral to the body part and a brain region selected from brain regions ipsilateral to the body part.

The brain wave detecting unit 10 detects biometric information in a brain region included in a movement-related region in the brain of an adult.

As a result, it is possible to perform training that causes a body part to function by selecting an appropriate selectable brain region in the brain of an adult.

The brain wave detecting unit 10 detects biometric information in a brain region included in a movement-related region and in a region other than the movement-related region including a sensory area in the brain of a child or an infant.

As a result, it is possible to perform training to cause the body part to function by extensive brain regions that have the possibility of being activated by training in the brain of a child or an infant.

The brain wave detecting unit 10 detects biometric information in a plurality of brain regions of the test subject attempting movement of the body part.

The control unit 20 determines, based on the brain waves detected by the brain wave detecting unit 10, the brain region(s), which has (have) been selected as a target associated with the body part from among a plurality of activated brain regions, by determining an activated state or activated states in the brain.

As a result, because an appropriate brain region or appropriate brain regions of the test subject, which activate(s) in response to a specific motion that will be performed in the training, is (are) selected, it is possible to perform the training for causing the body part to function more efficiently.

The output unit includes an assisting device (movement assisting unit 30) that assists movement of the body part.

As a result, by feeding back a kinesthetic sensation of the body part to the brain, it is possible to induce plasticity of the brain.

The output unit includes a display device (the display of the information output unit 25) that displays whether or not the activated state in the brain conforms to the predetermined condition.

As a result, it is possible to easily perform the training that causes the body part to function.

The output unit includes a perceptual stimulator that applies a perceptual stimulus to the test subject if the activated state(s) in the brain do(es) not conform to the predetermined condition.

As a result, the retention rate of the training effect in the test subject can be increased.

EXPLANATION OF THE REFERENCE NUMERALS

1 Biometric information processing device, 10 Brain wave detecting unit, 20 Control unit, 21 CPU, 21a Biometric information acquisition unit, 21b Brain activation state determination unit, 21c Movement assistance control unit, 22 ROM, 23 RAM, 24 Information input unit, 25 Information output unit, 26 Storage unit, 27 Communication unit, 30 Movement assisting unit, 31 Body support part, 32 Arm part, 32a, 32b Belt member, 33 Coupling part, 34 Actuator

The invention claimed is:
1. A method of treating a patient having a hemiplegic shoulder and elbow, comprising:

monitoring brain waves in the somatosensory motor cortex of regions of the brain of the patient that are ipsilateral and contralateral to the hemiplegic shoulder and elbow using a biometric information detecting unit attached to the patient's scalp while showing the patient imagery designed to cause the patient to imagine moving the hemiplegic shoulder and elbow, calculating event-related desynchronization (ERD) values from the monitored brain waves using an information processing device, and in response to satisfying at least two predetermined conditions, causing a movement assisting device connected to the hemiplegic shoulder and elbow to execute a predetermined motion that assists movement of the hemiplegic shoulder and elbow, wherein the at least two predetermined conditions include (i) a determination that at least one of the calculated ERD values in the region of the brain of the patient that is ipsilateral to the hemiplegic shoulder and elbow has exceeded a first predetermined threshold while the imagery is being shown to the patient and (ii) a determination that at least one of the calculated ERD values in the region of the brain contralateral to the hemiplegic shoulder and elbow does not exceed a second predetermined threshold of activation level.

2. The method according to claim 1, wherein the monitored brain waves have a principal component in the range of 8-13 Hz.

3. The method according to claim 1, wherein the first predetermined threshold is 30% or more.

4. The method according to claim 1, wherein the movement assisting device is an upper limb exoskeleton robot.

5. The method according to claim 1, wherein the biometric information detecting unit comprises a plurality of electrodes arranged in a matrix over the patient's scalp.

6. The method according to claim 1, further comprising:
outputting a perceptual stimulus from a perceptual stimulator to the patient in response to a determination that none of the calculated ERD values in the region of the brain of the patient that is ipsilateral to the hemiplegic shoulder and elbow has exceeded the first predetermined threshold while the imagery is being shown to the patient.

7. The method according to claim 1, further comprising:
showing on a display device whether any of the calculated ERD values in the region of the brain of the patient that is ipsilateral to the hemiplegic shoulder and elbow has exceeded the first predetermined threshold while the imagery is being shown to the patient.

8. The method according to claim 1, wherein the information processing device comprises a central processing unit and memory.

9. A non-transitory computer readable medium storing a program that, when executed, causes a computer controlling a biometric information processing device that processes biometric information of a subject to:

monitor brain waves in the somatosensory motor cortex of regions of the brain of a patient that are ipsilateral and contralateral to a hemiplegic shoulder and elbow of the patient while showing the patient imagery designed to cause the patient to imagine moving the hemiplegic shoulder and elbow, calculate event-related desynchronization (ERD) values from the monitored brain waves, and in response to satisfying at least two predetermined conditions, cause a movement assisting device connected to the hemiplegic shoulder and elbow to execute a predetermined motion that assists movement of the hemiplegic shoulder and elbow, wherein the at least two predetermined conditions include (i) a determination that at least one of the calculated ERD values in the region of the brain of the patient that is ipsilateral to the hemiplegic shoulder and elbow has exceeded a predetermined threshold while the imagery is being shown to the patient and (ii) a first determination that at least one of the calculated ERD values in the region of the brain contralateral to the hemiplegic shoulder and elbow does not exceed a second predetermined threshold of activation level.

10. The non-transitory computer readable medium according to claim 9, wherein the monitored brain waves have a principal component in the range of 8-13 Hz.

11. The non-transitory computer readable medium according to claim 9, wherein the first predetermined threshold is 30% or more.

12. A biometric information processing device comprising:

a biometric information detecting unit configured to monitor brain waves in the somatosensory motor cortex of regions of the brain of a patient that are ipsilateral and contralateral to a hemiplegic shoulder and elbow of the patient while showing the patient imagery designed to cause the patient to imagine moving the hemiplegic shoulder and elbow, an information processing device configured to calculate event-related desynchronization (ERD) values from the monitored brain waves, and a movement assisting device configured to be connected to the hemiplegic shoulder and elbow and to, in response to at least two predetermined conditions being satisfied, execute a predetermined motion that assists movement of the hemiplegic shoulder and elbow, wherein the at least two predetermined conditions include (i) a determination that at least one of the calculated ERD values in the region of the brain of the patient that is ipsilateral to the hemiplegic shoulder and elbow has exceeded a first predetermined threshold while the imagery is being shown to the patient and (ii) a determination that at least one of the calculated ERD values in the region of the brain contralateral to the hemiplegic shoulder and elbow does not exceed a second predetermined threshold of activation level.

13. The biometric information processing device according to claim 12, wherein the biometric information detecting unit is configured to monitor brain waves having a principal component in the range of 8-13 Hz.

14. The biometric information processing device according to claim 12, wherein the first predetermined threshold is 30% or more.

15. The biometric information processing device according to claim 12, wherein the movement assisting device is an upper limb exoskeleton robot.

16. The biometric information processing device according to claim 12, wherein the biometric information detecting unit comprises a plurality of electrodes configured to be arranged in a matrix over a scalp of the patient.

17. The biometric information processing device according to claim 12, further comprising a perceptual stimulator configured to output a perceptual stimulus to the patient in response to a determination that none of the calculated ERD values in the region of the brain of the patient that is ipsilateral to the hemiplegic shoulder and elbow has exceeded the first predetermined threshold while the imagery is being shown to the patient.

18. The biometric information processing device according to claim 12, further comprising a display device configured to show whether any of the calculated ERD values in the region of the brain of the patient that is ipsilateral to the hemiplegic shoulder and elbow has exceeded the first predetermined threshold while the imagery is being shown to the patient.

19. The biometric information processing device according to claim 12, wherein the information processing device comprises a central processing unit and memory.

20. The biometric information processing device according to claim 19, wherein:
- the movement assisting device is an upper limb exoskeleton robot, and
- the biometric information detecting unit comprises a plurality of electrodes configured to be arranged in a matrix over a scalp of the patient.

\* \* \* \* \*